United States Patent [19]

Hagel et al.

[11] Patent Number: 5,615,684

[45] Date of Patent: Apr. 1, 1997

[54] MEDICAL DEVICE FOR DETECTING HEMODYNAMIC CONDITIONS OF A HEART

[75] Inventors: Pia Hagel, Sollentuna; Kjell Noren, Solna; Kurt Hoegnelid, Västerhaninge, all of Sweden

[73] Assignee: Pacesetter AB, Solna, Sweden

[21] Appl. No.: 429,614

[22] Filed: Apr. 27, 1995

[30] Foreign Application Priority Data

May 6, 1994 [SE] Sweden .................................. 9401578

[51] Int. Cl.$^6$ .................................................. A61B 5/021
[52] U.S. Cl. .................................................. 128/670
[58] Field of Search .................................. 128/670–675, 128/691–693, 713, 734; 607/6, 17, 18, 23

[56] References Cited

U.S. PATENT DOCUMENTS

| | | |
|---|---|---|
| 4,453,551 | 6/1984 | Andersen et al. . |
| 4,870,974 | 10/1989 | Wang . |
| 5,058,599 | 10/1991 | Andersen . |
| 5,265,617 | 11/1993 | Verrier et al. . |
| 5,289,823 | 3/1994 | Eckerle ............................... 128/691 X |
| 5,316,004 | 5/1994 | Chesney et al. .................... 128/691 X |
| 5,368,040 | 11/1994 | Carney ................................. 128/672 X |

*Primary Examiner*—Angela D. Sykes
*Assistant Examiner*—Samuel Gilbert
*Attorney, Agent, or Firm*—Hill, Steadman & Simpson

[57] ABSTRACT

A device for detecting hemodynamic conditions in a heart, in particular conditions corresponding to dangerous arrhythmias contains a sensing unit for a physiological variable, such as blood pressure, the unit emitting a signal on the basis of the variable having an average value, a signal conditioning unit connected to the sensing unit, a calculation unit connected to the signal conditioning unit and a comparator after the calculation unit. The calculation unit is devised to calculate a variability measure relative to the signal's average value, the variability measure being correlated to average blood pressure, and the variability measure is compared in the comparator to an adjustable threshold value corresponding to a specific hemodynamic condition, whereupon the comparator emits an indication signal when the variability measure falls below the threshold value.

10 Claims, 1 Drawing Sheet

MEDICAL DEVICE FOR DETECTING HEMODYNAMIC CONDITIONS OF A HEART

BACKGROUND OF THE INVENTION

1. Field of the Invention

The present invention relates to a medical device for detecting hemodynamic conditions of a heart, in particular conditions corresponding to dangerous arrhythmias.

2. Description of the Prior Art

An electromedical implant for electrical treatment of a heart which may exhibit dangerous arrhythmias must be capable of identifying the presence of these conditions. Detection of, e.g., ventricular fibrillation (VF), however, is associated with difficulties in the prior art. One such difficulty is that the detection of VF from, e.g., the ECG signal (the heart's depolarization signal) requires knowledge of the ECG signal's morphology, as illustrated in U.S. Pat. No. 5,058,599.

This patent discloses a method and a device for detecting a dangerous heart condition wherein a sequence of abnormal events is detected among a plurality of normal events in an electric signal, especially in a depolarization signal in the heart. According to this known method, a plurality of signal parameters, typical of the event to be detected, are identified. One such parameter can be, e.g., the signal's derivative within a special tracing segment. After normal and abnormal events are extracted from the signal, a statistical calculation, based on all recorded events for a sequence of the identified signal parameters, is performed. or example, standard deviation is calculated, and this value is compared to a predefined threshold value. If the value for the standard deviation exceeds the threshold value, this indicates the presence of an abnormal condition.

In order to come to grips with this difficulty and to achieve an ability to select reliable triggering points in an individual signal tracing in order to identify, e.g., the tracing slope during a specific interval, use of the ECG signal according to the procedure shown in U.S. Pat. No. 4,453,551 could be a solution.

A device and a method for analyzing and distinguishing dangerous fibrillation conditions from the heart's normal sinus rhythm as well as from other conditions in the heart, such as ventricular tachycardia, are also known from U.S. Pat. No. 4,453,551. This is achieved by the study of a number of tests performed on a extracorporeally recorded ECG signal. Before these tests can be performed, the signal is sampled, filtered and standardized. In standardization, the amplitude of the signal, which varies greatly from one patient to another, is standardized (normalized). According to one of these tests, the ratio between the energy in an ECG signal, above and below a zero level, is calculated in a time window. In ventricular tachycardia or sinus rhythm which, in contrast to fibrillation, displays a regular ECG signal, the calculated energy ratios are largely constant in a series of consecutive time windows, making it possible to distinguish tachycardia from fibrillation. An alternative calculation method for this test is to calculate and study variations in the energy ratios for a series of consecutive time windows.

Another device in which the ECG signal is utilized for detecting ventricular fibrillation and ventricular tachycardia is disclosed in U.S. Pat. No. 4,870,974. In this known device, the heart's hemodynamic state is studied with the aid of pressure signals, in addition to a study of the ECG signal's tracing morphology. For the pressure signal, the time that the measured pressure is below a specific level is determined, with different threshold values are for e.g. fibrillation and tachycardia being used in this determination. As with the device according to U.S. Pat. No. 5,058,599, certain parameters must also be identified in U.S. Pat. No. 4,870,974 from an individual signal tracing. For the pressure signal, a reference level, for example, must be identified from the signal tracing for detection to work.

SUMMARY OF THE INVENTION

An object of the present invention is generally to set forth a simplified and improved device for detecting hemodynamic conditions.

More specifically, the aim of the invention is to achieve more reliable detection of dangerous, hemodynamically unstable conditions, such as tachycardia and fibrillation. As will be described below, changes in the average level of blood pressure in the heart are studied indirectly.

If the average blood pressure in the heart drops, e.g. as the result of ventricular tachycardia or fibrillation, this indicates that the heart's pumping capacity has declined and that the heart is no longer capable of supplying vital organs, such as the brain, with oxygenated blood; damage can then occur very rapidly as a result.

The object is achieved in accordance with the principles of the present invention a device having a sensor which measures a physiological variable and which emits an electrical signal corresponding to the physiological variable. A signal conditioning unit acts on the signal emitted by the physiological sensor, and produces an edited signal, the edited signal being supplied to a calculation unit. The calculation unit calculates a variability measure, which is mathematically related to, but is not the same as, the average value of the signal emitted by the sensing unit, the variability measure being correlated to average blood pressure. The variability measure is then compared in the comparator to an adjustable threshold value corresponding to a specific hemodynamic condition, whereupon the comparator emits an indication signal if the variability measure falls below the threshold value.

The physiological sensor may be a sensor which senses blood pressure, or an impedance sensor, or a sensor which senses both blood pressure and impedance.

As will be apparent, the invention therefore does not require any analysis of the morphology of the signal dependent on the physiological variable. As used herein, therefore, the term "variability measure" means a mathematical calculation made on the edited signal without morphology analysis.

The invention is based on the discovery of a correlation between a variability measure (e.g. the rectified average value, the standard deviation or the root mean square value (RMS)), related to the average value of a signal generated according to a sensed physiological variable, and average blood pressure in the heart.

A decrease in the variability measure has been found to be correlated to a drop in the level of average blood pressure. When the variability measure falls below a given level, this indicates the presence of a dangerous condition.

For a continuous, consistently varying signal with a constant amplitude, the signal's variability measure (e.g. standard deviation, rectified average value or RMS), according to general statistical theory, must be constant, independent of signal frequency. For example, standard deviation is the same for sinus signals with the frequencies f and 5f. As regards amplitudes, halving the amplitude, for example, also halves the variability measure. A consequence of these correlations is then that the amplitude of a signal, which normally does not change its morphology but displays a varying frequency, can be calculated by determining the variability measure. If the amplitude of the signal changes, these changes can be determined, since the variability measure displays similar changes.

When these factors are applied to a device according to the invention for determining average blood pressure, this means that the device will work independently of the prevailing heart rate and, can thus detect dangerous tachyarrhythmias which can even occur at heart rates under 150 beats/min, since heart rate alone is not a measure of this tachyarrhythmias.

The signal generated on the basis of a sensed physiological variable must retain its morphology for the method to work according to the aforementioned considerations. When this condition is met, the device according to the invention provides a method for detecting dangerous ventricular tachyarrhythmias.

The signal can have an unchanged morphology, even in fibrillation in which heart rates can exceed 400 beats/min, so the invention is also applicable to the detection of fibrillation.

Animal experiments have surprisingly shown that a variability measure, related to the average value for a signal generated according to a sensed physiological variable and which displays changes in morphology, is correlated to average blood pressure in the heart.

This means that the study of the change in a variability measure which is the average value for a signal generated on the basis of a sensed physiological variable makes it possible to detect dangerous ventricular tachycardia and ventricular fibrillation, both with a stable signal morphology and an unstable signal morphology, with greater certainty and with simpler equipment than has previously been possible.

According to a preferred embodiment, the variability measure is calculated for a specific period of time in a time window with a predefined duration. This value for the variability measure is compared to a first adjustable threshold value, representing a detection threshold for dangerous tachycardia, and to a second adjustable threshold value, representing a detection threshold for fibrillation, the first value being larger than the second. An indication signal is emitted when a value for the variability measure falls below any of these threshold values so suitable therapy can be instituted.

DESCRIPTION OF THE PREFERRED EMBODIMENTS

The same or similar components in the both Figures have the same reference designations.

The invention will be described herein in the context of a medical device in the form of a tachycardia-terminating pacemaker. As will be understood by those knowledgeable in the art, however, no limitation to this application is intended. The device according to the invention could also be used in, e.g., a defribillator or with a device for sensing hemodynamic conditions in the heart for diagnostic purposes. The device can be applied to both implanted an extracorporeal medical devices.

Figure 1:
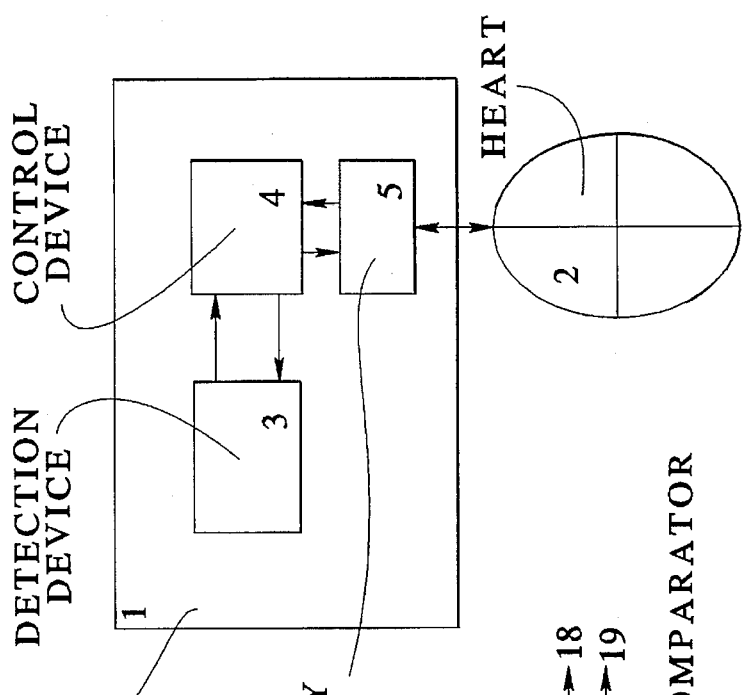
FIG. 1 is a block diagram of a medical device which contains the detection device according to the invention.

FIG. 1 shows a medical device 1 connected to a heart 2. The medical device 1 contain a detection device 3 or sensing a physiological variable and processing and evaluating a signal 10 which depends on the variable, a programmable control device 4 for controlling and coordinating the parts in the device 1 and a therapy stage 5 for instituting suitable therapy for the heart 2. As previously noted, the medical device 1 is exemplified as a tachycardia-terminating pacemaker, whereby the therapy stage 5 is a pulse generator, controlled by the control device 4, for stimulating the heart 2 with stimulation pulses. The therapy stage 5 is of conventional design and will not be further described herein, since it does not contribute to an understanding of the detection device according to the invention.

Figure 2:
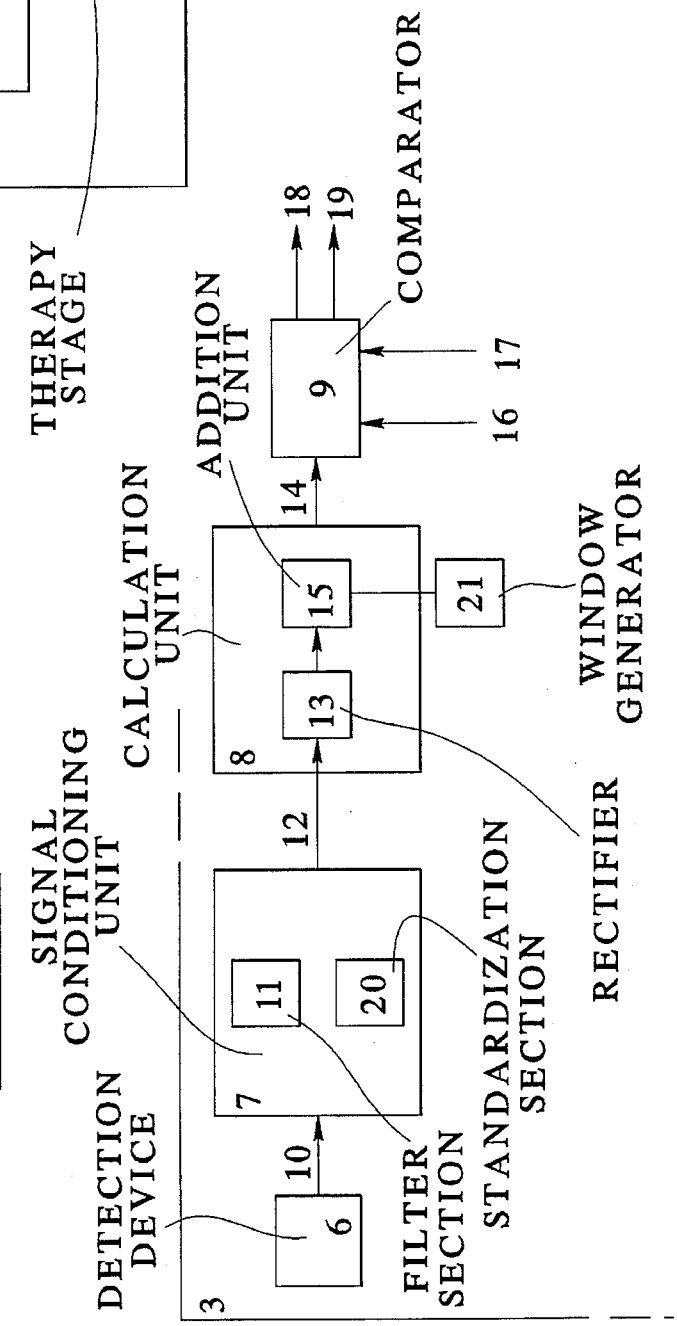
FIG. 2 is a block diagram of the detection device according to the invention.

FIG. 2 is a block diagram of the detection device 3. According to the invention, it contains a sensing unit 6, a signal conditioning unit 7, a calculation unit 8 and a comparator 9. The sensing unit 6 for the physiological variable sends the signal 10, which depends on the variable, to the signal conditioning unit 7 in which the signal can be filtered in a filter section 11. The signal 12 emitted by the signal conditioning unit 7 is sent to the calculation unit 8 in which a variability measure 14 is calculated for the signal 12 by an addition unit 15. The signal 12 can also be rectified in a rectifier 13 in the calculation unit 8 before being sent to the addition unit 15. The variability measure 14 is compared in the comparator 9 to a threshold values respectively supplied via lines 16 and 17, and the comparator emits respective indication signals 18 and 19 when the variability measure 14 falls below the threshold values from lines 16 and 17.

According to a preferred embodiment, the signal conditioning unit 7 also contains, in addition to the filter section 11, a standardization section 20, formed by an amplifier, for standardizing (normalizing) the signal. According to this preferred embodiment, a window generator 21 is additionally connected to the addition unit 15 which generates a time window with a predefined duration during which the variability measure 14 is calculated.

The sensing unit 6 can be a pressure sensor or an impedance sensor. Both a pressure sensor and an impedance sensor can also be used simultaneously.

The pressure sensor is placed in the right ventricle and can consist of e.g. a piezoelectric crystal. Pressure measurement with a piezocrystal is a fast, well-tried measurement method which supplies easily interpreted measurement values. An additional advantage is that the absolute level of pressure can also be determined. Disadvantages in measuring pressure are the circumstance that the sensor's output signal is very weak and a special electrode is required to perform the measurements. Impedance measurement is performed between two points in the right ventricle with the aid of a standard electrode in which measurement is between the electrode tip and a ring on the electrode cable at a distance from the electrode tip. Measurement is performed with the alternating current method (AC method) to prevent the polarization effects occurring at the emission of direct current (DC method). The measurement current could be e.g. a continuous square wave with an amplitude of 10 µA and a frequency of 4 kHz. A signal representing impedance is sent from the sensing unit 6 to the signal conditioning unit 7. Measurement of impedance in the heart is a method well-known to those skilled in the a and will not be further described here.

The signal 10 from the sensing unit 6 is sent to the signal conditioning unit 7 in which the signal can be filtered in the filter section 11. Whether the signal 10 is to be filtered depends on the variability measure selected for calculation. The different variability measures used are the rectified average value (i.e. the average value of the rectified signal), standard deviation and the RMS value. When the rectified average value or the RMS value are calculated, the average value for the (unrectified) signal 10 must be zero, i.e. any direct current level for the signal 1 is filtered out. This is achieved when the filter section 11 filters out signal components less than e.g. 0.2 Hz. The average value for the signal does not have to be zero for calculation of standard deviation, so filtering out the DC level is not necessary.

Filtering out high frequency noise signals in the signal is often desirable. This is achieved when the filter section 11 filters out signals higher than, e.g., 15 Hz.

Filtration has very little effect on the morphology of pressure or impedance signals. According to a preferred embodiment of the invention, the signal is standardized in the standardization section 20 after filtration. This section consists of an amplifier which amplifies the signal with appropriate gain so variations in signal amplitude are kept within specific limits. The filtered and standardized signal is then sent to the calculation unit 8 in which a variability measure 14 is calculated by the addition unit 15 for the rectified signal.

Calculations can be made either on a continuous signal or on a discrete signal. The calculations entail integration of the signal, in the case of a continuous signal, and addition of discrete values, in the case of a discrete signal. Calculations in the addition unit 15 also include division, squaring ad root extraction according to the calculation method selected. If the calculations are to be made from the discrete signal, the continuous signal is sampled in the signal conditioning unit 7 before the signal is sent to the addition unit 15. Sampling is performed at a sufficiently high frequency, e.g. 10 Hz to 100 Hz, with a view to the signal's frequency, all according to techniques familiar to those skilled in the art and need not be described herein. According to the preferred embodiment, the variability measure 14 is calculated in a time window with a predefined duration. An appropriate time has proved to be about 6 seconds. The duration of the time window is selected so calculations are made over a number of heart cycles with normal heart rhythm. When a duration of about 6 seconds is chosen, at least one complete respiratory cycle is also covered.

The time windows can be arrayed in many different ways. The time window can be isolated, with a long interval to the next window, or the interval between consecutive time windows can be of the same duration as the duration of the time window. A new time window can immediately follow a preceding window, without any interval between windows, and a new calculation made for each window. A new calculation can be made after each half window within each full time window, and the time window can also he floating. For a discrete signal this means that a new calculation is made after every sampling. Another possibility is for calculations to be performed over a number of time windows with a new calculation made in each time window.

The following table shows how the different variability measures are calculated for a continuous signal and for a discrete, sampled signal:

|  | Rectified average value | Standard deviation | Root mean square (RMS) |
| --- | --- | --- | --- |
| Continuous signal | $\frac{1}{T_w} * \int_0^{T_w} |S(t)|dt$ | $\sqrt{\frac{1}{T_w} \int_0^{T_w} S^2(t)dt}$ | $\sqrt{\frac{1}{T_w} \int_0^{T_w} S^2(t)dt}$ |
| Discrete, sampled signal | $\frac{1}{N} * \sum_{i=1}^{N} |S_i|$ | $\sqrt{\frac{1}{N-1} \sum_{i=1}^{N} S_i^2}$ | $\sqrt{\frac{1}{N} \sum_{i=1}^{N} S_i^2}$ | wherein $T_w$ is the duration of the time window, with a start at time $t=0$, $S(t)$ is the continuous signal, $S_i$ is sample no. i in the continuous signal taken at time $t_i$, $i = 1, 2, \ldots N$, and N is the number of samples in the time window. The table assumes the average value of the signal is $S_{avg}=0$.

As noted above, the average value does not have to be zero for calculation of standard deviation. The complete equation for the standard deviation of a discrete signal is:

$$S_{stdv} = \sqrt{\frac{1}{N-1} \sum_{i=1}^{N} (S_i - S_{avg})^2}$$

in which $S_{avg}$ is obtained from the calculation:

$$S_{avg} = \frac{1}{N} \sum_{i=1}^{N} S_i$$

for discrete signals.

In an analogous manner, the standard deviation of a continuous signal can be calculated when the average value is other than zero.

For calculation of the rectified average value, the signal is rectified before calculations are performed in the addition unit 15. No rectification of the signal has to be performed if standard deviation or the RMS value are calculated instead.

The variability measure calculated in the addition unit 15 is then compared in the comparator 9 to a threshold values supplied by lines 16 and 17 for a hemodynamic state. According to the preferred embodiment, the variability measure 14 is compared to a first adjustable threshold value from line 16 and a second adjustable threshold value from line 17, and the comparator 9 emits a first indication signal 18 indicating the presence of ventricular tachycardia when the variability measure 14 falls below the first threshold value from line 16. The comparator 9 emits a second indication signal 19 indicating the presence of ventricular fibrillation when the variability measure 14 falls below the second threshold value from line 17, the first value on line 16 being greater than the second value on line 17.

The indication signals 18 and 19 emitted by the comparator 9 are sent to the control device 4 which is arranged to take steps relevant to the indication signals to initiate and control the administration of appropriate therapy by the therapy stage 5.

Calculations for a continuous signal can also be performed with a simple averaging circuit, consisting of a resistor and capacitor, with appropriately selected component values, connected to a reference level at which the signal's average value is determined between the resistor and the capacitor. No window generator is required in this simple averaging procedure.

It is not necessary for signal standardization to take in the signal conditioning unit's standardization section 20. Instead, standardization can be performed by adapting the threshold values on lines 16 and 17 in the comparator 9 in some manner appropriate to the magnitude of the variability measure.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for detecting hemodynamic conditions of a heart, comprising:

sensor means for sensing a physiological variable in a living subject and for emitting an electrical signal dependent of said physiological variable, said electrical signal having an average value;

signal editing means for editing said electrical signal to produce an edited signal;

calculating means supplied with said edited signal for calculating a variability measure of the edited sign related to but different from said average value of said electrical signal and correlated to average blood pressure of said living subject; and comparator means for comparing said variability measure to a threshold selectable dependent on a selected hemodynamic condition, for emitting an indication signal indicating the presence of said selected hemodynamic condition in said living subject when said variability measure falls below said threshold.

2. A device as claimed in claim 1 wherein said signal editing means comprises means for filtering said electrical signal and for standardizing said electrical signal.

3. A device as claimed in claim 1 wherein said calculating means comprises time window generator means for generating a time window with a pre-determined duration within which said variability measure is calculated.

4. A device as claimed in claim 1 wherein said calculating means comprises a rectifier for rectifying said edited signal and an addition unit for calculating said variability measure of the rectified signal.

5. A device as claimed in claim 1 wherein said calculating means comprises means for calculating the root mean square of said edited signal.

6. A device as claimed in claim 1 wherein said calculating means comprises means for calculating the standard deviation of said edited signal.

7. A device as claimed in claim 1 wherein said comparator means comprises means for comparing said variability measure to a first threshold selected dependent on a first hemodynamic condition and for comparing said variability measure to a second threshold, different from said first threshold, dependent on a second hemodynamic condition.

8. A device as claimed in claim 1 wherein said sensor means comprises a pressure sensor.

9. A device as claimed in claim 1 wherein said sensor means comprises an impedance sensor.

10. A device as claimed in claim 1 wherein said sensor means comprises means for measuring blood pressure and impedance in said living subject.

* * * * *